(12) United States Patent
Park et al.

(10) Patent No.: US 10,668,184 B2
(45) Date of Patent: Jun. 2, 2020

(54) MAGNETICALLY ACTUATED ARTICULAR CARTILAGE REGENERATION SYSTEM

(71) Applicant: INDUSTRY FOUNDATION OF CHONNAM NATIONAL UNIVERSITY, Gwangju (KR)

(72) Inventors: Suk Ho Park, Gwangju (KR); Jongoh Park, Gyeonggi-do (KR); Ji Won Han, Gwangju (KR); Byung Jeon Kang, Gwangju (KR); Gwangjun Go, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 58 days.

(21) Appl. No.: 16/097,714

(22) PCT Filed: Oct. 26, 2017

(86) PCT No.: PCT/KR2017/011901
§ 371 (c)(1),
(2) Date: Oct. 30, 2018

(87) PCT Pub. No.: WO2018/080191
PCT Pub. Date: May 3, 2018

(65) Prior Publication Data
US 2019/0167847 A1  Jun. 6, 2019

(30) Foreign Application Priority Data
Oct. 26, 2016 (KR) .................. 10-2016-0139848

(51) Int. Cl.
*A61N 2/06* (2006.01)
*A61L 27/38* (2006.01)
(Continued)

(52) U.S. Cl.
CPC ............ *A61L 27/3817* (2013.01); *A61B 6/12* (2013.01); *A61B 6/50* (2013.01); *A61B 6/505* (2013.01); *A61B 6/5217* (2013.01); *A61F 2/30* (2013.01); *A61K 35/32* (2013.01); *A61K 41/00* (2013.01); *A61K 47/6923* (2017.08); *A61K 47/6929* (2017.08); *A61L 27/18* (2013.01); *A61L 27/3834* (2013.01); *A61L 27/3852* (2013.01); *A61L 27/50* (2013.01); *A61L 27/56* (2013.01);
(Continued)

(58) Field of Classification Search
CPC ............ A61L 2430/06; A61L 27/3817; A61L 27/3834; A61L 27/3852; A61L 27/56; A61F 2002/30766; A61F 2/30756; A61N 2/002; A61N 2/02; A61N 2/06
See application file for complete search history.

(56) References Cited

FOREIGN PATENT DOCUMENTS

| KR | 10-0799060 | 1/2008 |
|---|---|---|
| KR | 2020120004971 | 7/2012 |

(Continued)

OTHER PUBLICATIONS

Go, Gwangjun etc., A Magnetically Actuated Microscaffold Containing Mesenchymal Stem Cells for Articular Cartilage Repair. Advanced Healthcare Materials. Jul. 5, 2017. vol. 6, No. 13, 1601378 (p. 1-10).

*Primary Examiner* — Christine H Matthews
(74) *Attorney, Agent, or Firm* — Mayer & Williams, PC; Stuart H. Mayer

(57) ABSTRACT

The present invention provides a magnetically-actuated articular cartilage regeneration system for efficiently and nonsurgically regenerating articular cartilage.

9 Claims, 10 Drawing Sheets

(51) Int. Cl.
  *A61N 2/02*    (2006.01)
  *A61L 27/56*   (2006.01)
  *A61K 41/00*   (2020.01)
  *A61K 35/32*   (2015.01)
  *A61N 2/00*    (2006.01)
  *A61B 6/12*    (2006.01)
  *A61B 6/00*    (2006.01)
  *A61K 47/69*   (2017.01)
  *A61F 2/30*    (2006.01)
  *A61L 27/50*   (2006.01)
  *A61L 27/58*   (2006.01)
  *A61L 27/18*   (2006.01)

(52) U.S. Cl.
  CPC .............. *A61L 27/58* (2013.01); *A61N 2/002* (2013.01); *A61N 2/004* (2013.01); *A61N 2/02* (2013.01); *A61N 2/06* (2013.01); *A61L 2400/12* (2013.01); *A61L 2430/06* (2013.01)

(56) References Cited

FOREIGN PATENT DOCUMENTS

| | | |
|---|---|---|
| KR | 1020140009968 | 1/2014 |
| KR | 10-2016-0031683 | 3/2016 |
| KR | 1020160028070 | 3/2016 |
| KR | 10-1627043 | 5/2016 |
| KR | 10-2015-0039997 | 6/2016 |
| WO | 2016/065205 A1 | 4/2016 |

MAGNETICALLY ACTUATED ARTICULAR CARTILAGE REGENERATION SYSTEM

TECHNICAL FIELD

The present invention relates to a magnetically-actuated articular cartilage regeneration system, and more specifically, to a magnetically-actuated articular cartilage regeneration system consisting of a composition for regenerating cartilage, an image-photographing unit, and a magnetic field forming unit for nonsurgically regenerating articular cartilage.

BACKGROUND ART

Presently, osteoarthritis is the most frequent disease that occurs in elderly people. For example, it occurs in 70% or more of the population over 65 years of age worldwide and over 24% of the population over 50 years of age in Korea. Osteoarthritis frequently occurs in the knees, pelvis, fingertip joints, etc. and it accompanies abnormal bones around the joints along with articular cartilage defects thereby resulting in deterioration and loss of articular functions. Joints have a relatively low density of stem cells and progenitor cells in the tissue and have no blood vessels. As a result, migration of chondrocytes from the periphery is limited after cartilage damage, and its regeneration ability is lower than other tissues. Stem cells involved in healing during cartilage damage are also regenerated into fibrous cartilage with weak mechanical properties or have limited regeneration ability. For these reasons, treatment of articular cartilage damage (e.g., arthritis) initially resorts to a conservative therapy such as drugs, physical therapy, etc., and in the absence of any progress of symptoms, to therapies such as arthroscopic surgery, replacement arthroplasty, etc. In the case of the regeneration therapy for articular cartilage damage using stem cells, stem cell transplantation by surgical methods (e.g., a microfracture surgery using biomaterials, autologous chondrocytes or matrix-based chondrocyte implantation, etc.) is performed. However, these existing methods of cell (i.e., chondrocytes and stem cells) implantation for cartilage regeneration have problems in performing a surgical method by exposing a defected area, or precisely locating a large amount of cells to a defected area of articular cartilage and maintaining the number of cells during a period of treatment. To remedy the above problems, a method where magnetic particles are inserted into stem cells and controlling the same to be directed toward a desired direction using an outer permanent magnet was proposed (Goki Kamei et al., *Am. J. Sports Med.*, 41(6): 1255-1264, 2013).

DISCLOSURE OF THE INVENTION

Technical Problem

However, the method of the above reference has problems in that it is costly due to power consumption because of the use of superconductors; it is difficult to maintain the cells located in the lesion for a long period of time; and magnetic particles directly inserted into stem cells act on the stem cells thereby affecting their proliferation, differentiation, etc.

The present invention has been made to solve the above problems, and an object of the present invention is to provide a magnetically-actuated articular cartilage regeneration system for efficiently and nonsurgically regenerating articular cartilage. However, the object is for illustration purpose only and the scope of the present invention is not limited by the same.

Technical Solution

According to an aspect of the present invention, provided is a composition for regenerating cartilage, which contains a microstructure of a magnetic substance and a cartilage-producing cell.

According to an aspect of the present invention, provided is a magnetically-actuated articular cartilage regeneration system, which includes the composition for regenerating cartilage; an image-photographing unit for imaging the composition for regenerating cartilage and a lesion after irradiating x-ray on a defected area of cartilage; and a magnetic field forming unit for transporting the composition for regenerating cartilage to the defected area of cartilage.

Advantageous Effects

According to an embodiment of the present invention as described above, a nonsurgical and efficient effect of cartilage regeneration can be embodied using a magnetically-actuated articular cartilage regeneration system. However, the scope of the present invention is not limited by such an effect.

MODE FOR CARRYING OUT THE INVENTION

Definition of Terms

Figure 1A:
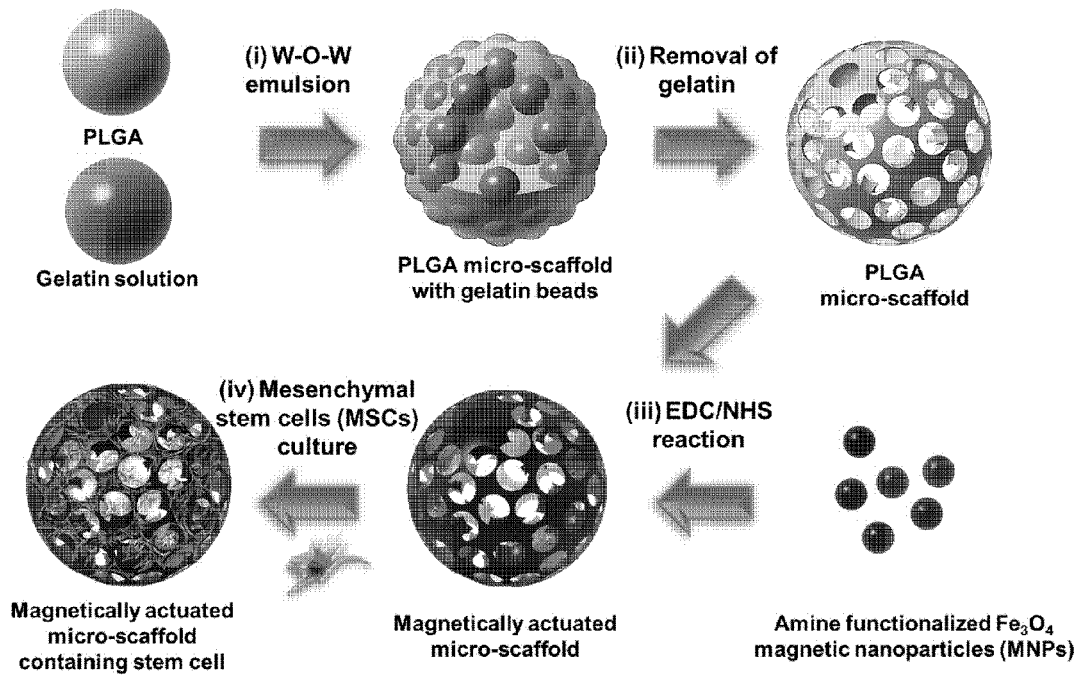
FIG. 1A shows a schematic diagram illustrating a manufacturing process of a microstructure for cartilage regeneration according to an embodiment of the present invention.

As used herein, the term "osteoarthritis", also called degenerative arthritis, is a disease which accompanies progressive loss of articular cartilage in local joints and secondary changes and symptoms related thereto, and it is a disease where joint-forming bones, ligaments, etc. are damaged due to progressive damages or degenerative changes of joint-protecting cartilage thereby causing inflammation and pain thereon.

As used herein, the term "magnetic field", which is also called magnetic flux, refers to a space where lines of magnetic force are spread out, that is, a space exerted by magnetism, such as the periphery of electric current or magnet and the surface of the Earth, etc.

As used herein, the term "microfracture surgery using biomaterials", which is an improved method of a microfracture surgery which was suitable for a short-term clinical study, refers to autologous matrix-induced chondrogenesis (AMIC) where bone marrow mesenchymal stem cells were allowed to leak out of a defected area and then the defected area is sutured with collagen; or autologous collagen-induced chondrogenesis (ACIC) where stem cells are fixed to a defected area using a biomaterial in the form of a gel.

As used herein, the term "chondrocyte implantation" refers to autologous chondrocyte implantation (ACI), where a defected area of cartilage is blocked with collagen or periosteum and then autologous chondrocytes cultured ex vivo are implanted thereto thereby inducing cartilage regeneration; and matrix-induced autologous chondrocyte implantation (MACI), where biomaterials containing autologous chondrocytes are implanted to a local area where it is difficult to apply periosteum.

DETAILED DESCRIPTION OF THE PRESENT INVENTION

According to an aspect of the present invention, provided is a composition for regenerating cartilage containing a microstructure, to which a magnetic substance and a cartilage-producing cell are attached.

In the above composition, the cartilage-producing cells may be, but are not limited to, chondrocytes or stem cells, and the stem cells may be bone marrow-derived stem cells, umbilical cord blood-derived stem cells, or adipose-derived stem cells, and dedifferentiated stem cells, embryo-derived stem cells, etc. may also be used.

In the above composition, the magnetic substance may be magnetic nanoparticles, and the magnetic nanoparticles may be amine-functionalized $Fe_3O_4$ nanoparticles. The amine-functionalization may be achieved by attaching polyethylenimine (hereinafter, PEI) to the magnetic nanoparticles, and the amine-functionalized $Fe_3O_4$ nanoparticles may be prepared by a covalent bond between PEI and a carboxyl group of the microstructure.

In the above composition, the microstructure may be a biocompatible polymer scaffold, and the biocompatible polymer scaffold may be a porous scaffold.

As used herein, the term "biocompatible polymer" refers to a polymer which has biocompatibility that does not induce any adverse effects with regard to a bio-organism in vivo among biodegradable polymers and non-biodegradable polymers, and more preferably a biodegradable polymer, but the biocompatible polymer is not limited thereto. The polymer may form a porous structure for the formation of a microstructure, and the biodegradable polymer may be a natural polymer or a synthetic polymer. The natural polymer may be collagen, hyaluronic acid, gelatin, or chitosan, and the synthetic polymer may be poly(lactic-co-glycolic acid) (PLGA), poly(glycolic acid) (PGA), poly(lactic acid) (PLA), poyethylene glycol (PEG), polyvinyl alcohol (PVA), polyethylene glycol (PEG), poly(N-2-hydroxypropyl methacrylamide), polyhydroxyalkanoic acid (PHA), polycaprolactone (PCL), poly(propylene fumarate), polyanhydride, polyacetal, or polycarbonate, poly(ortho ester). The non-biodegradable polymer may be polyester, Teflon®, PET, nylon, polypropylene, or polystyrene.

The porous scaffold may be prepared by various methods, for example, a solvent evaporation method, a polymerization method, a seed swelling method, a sinter method, a synthesis method, a phase separation method, a spray drying method, a melt dispersion method, etc. (Cai et al., *Int. J. Nanomedicine.*, 8: 1111-1120, 2013). In an embodiment of the present invention, the porous scaffold was prepared by the solvent evaporation method.

The porous scaffold may be adjusted to have a diameter of 200-800 μm, and a pore size of the surface and interior of 20-200 μm.

In the above composition, the three-dimensional embryoid bodies of the cartilage-producing cells may be naturally formed when they are cultured in a culture container for three-dimensional culture of cells having conical grooves instead of a conventional plate culture container.

In the above composition, the magnetic substance may be uptaken into the cartilage-producing cell, and may be those which are attached to the surface of the cartilage-producing cell or the polymer scaffold by a covalent bond or non-covalent bond. The uptake of the magnetic substance into the cartilage-producing cell may be naturally achieved by phagocytosis of the cartilage-producing cell when the cartilage-producing cell are cultured in a medium containing the magnetic substance.

According to another aspect of the present invention, provided is a magnetically-actuated articular cartilage regeneration system, which includes: the composition for regenerating cartilage; an image-photographing unit for imaging the composition for regenerating cartilage and a lesion after irradiating x-ray on a defected area of cartilage; and a magnetic field forming unit for transporting the composition for regenerating cartilage to the defected area of cartilage.

In the magnetically-actuated articular cartilage regeneration system, the magnetic field forming unit may be a coil-type or a wearable-type, and the magnetic field formation of the magnetic field forming unit may be by a soft magnet, permanent magnet, or electromagnet. In particular, the permanent magnet may be ferrite, neodymium, alnico, samarium cobalt, or rubber magnet.

In the magnetically-actuated articular cartilage regeneration system, the cartilage-producing cell may be a chondrocyte or a stem cell, and the stem cell may be a bone marrow-derived stem cell, an umbilical cord blood-derived stem cell, or an adipose-derived stem cell.

The examples of the present invention are provided to allow those skilled in the art to more fully understand the present invention, and the following examples may be modified into various other forms, and the scope of the present invention is not limited to the following Examples. Rather, these examples are provided so that the present disclosure will be more faithful and complete, and will fully convey the scope of the invention to those skilled in the art. Additionally, in the drawings, the thickness and size of each layer are exaggerated for convenience and clarity of explanation.

Throughout the specification, when one constituting element (e.g., membrane, area, substrate, etc.) is referred to be located as being "on", "connected", "stacked", or "coupled" to another constituting element, it may be interpreted that the one constituting element is directly in contact with the another constitution element by being "on", "connected", "stacked", or "coupled", or still other constituting elements to be interposed therebetween may be present. In contrast, when one constituting element is referred to be located as being "directly on", "directly connected", or "directly coupled" to another constituting element, it is interpreted that no other constituting elements to be interposed therebetween are present. The same reference numeral indicates the same element. As used herein, the term "and/or" includes any one of the listed items and one or more combinations of the listed items.

In the present specification, the terms first, second, etc. are used to describe various elements, components, regions, layers and/or parts, but it is apparent that the elements, components, regions, layers and/or parts should not be limited to these terms. These terms are used only to distinguish one element, component, region, layer or part from another region, layer, or part. Accordingly, a first element, component, region, layer, or part described below may refer to a second element, component, region, layer, or part without departing from the teachings of the present invention.

Additionally, relative terms such as "above" or "over" and "below" or "under" may be used herein to describe the relationship of certain elements to other elements as illustrated in the figures. It may be understood that relative terms are intended to encompass different orientations of the device in addition to the orientation depicted in the figures. For example, in the drawings, when a device is turned over, the elements illustrated as being on the upper surface of other elements will have orientations on the lower surface of the other elements. Therefore, the term "above" exemplified may encompass both orientations of "above" and "below" depending on a particular direction in the figures. If an element is directed to a different orientation (rotated 90 degrees with respect to the other orientation), the relative descriptions used herein can be interpreted accordingly.

The terms used herein are for the purpose of describing particular examples only and are not intended to limit the scope of the invention. As used herein, a singular form may include a plural form unless the context clearly indicates otherwise. Additionally, when used in the present invention, "comprise" and/or "comprising" specify the presence of stated features, integers, steps, operations, members, elements, and/or groups thereof, but do not preclude the presence or addition of one or more other features, integers, operations, members, elements, and/or groups.

MODES FOR CARRYING OUT THE INVENTION

Hereinafter, examples of the present invention will be described with reference to the drawings schematically showing ideal embodiments of the present invention. In the figures, for example, variations in the shape illustrated may be expected, depending on the manufacturing technique and/or tolerance. Accordingly, the examples of the present invention should not be construed as being limited to the specific shapes of the regions illustrated herein, but should include, for example, changes in shape resulting from manufacture.

FIG. 1*a* schematically shows a process for manufacturing a microstructure to which magnetic substances and cells for cartilage regeneration are attached, according to an embodiment of the present invention. As shown in FIG. 1A, a microstructure to which magnetic substances and cells for regenerating cartilage are attached in such a form that cells are attached to pores within the PLGA-micro-scaffold, can be manufactured by manufacturing a PLGA micro-scaffold, where gelatin beads are incorporated, by forming a W-O-W emulsion along with gelatin beads after selecting a biocompatible polymer as PLGA; manufacturing a PLGA micro-scaffold by removing the gelatin; forming a covalent bond between amine-functionalized magnetic nanoparticles with PEI and the PLGA micro-scaffold through the EDC/NHS reaction; and three-dimensional culturing the mesenchymal stem cells along with the PLGA micro-scaffold to which magnetic particles are attached. However, the method is for illustrative purpose and a microstructure to which the magnetic nanoparticles and cells for cartilage regeneration are attached can be manufactured by other various methods, for example, by attaching magnetic nanoparticles and cells for cartilage regeneration to a microstructure manufactured through a method such as electrospinning, etc. The present inventors have manufactured a PLGA-based microstructure by the method as described above, and as a result of photographing the same by a scanning electron microscope, it was confirmed that the microstructure manufactured as described above has a spherical shape as shown in FIG. 1B. Furthermore, the microstructure formed as described above was shown to have a diameter of 269.83±10.982 µm, a diameter of the surface pore of 37.68±7.55 µm, and a diameter of the inner pore of 40.12±7.45 µm, thus satisfying the requirements of a microstructure as a cell transporter (a diameter of 100 m to 500 µm and a pore size of 20 m or greater) (see FIGS. 1C to 1E). Since the microstructure to which cells for cartilage regeneration are attached contains a large amount of magnetic substances along with the cells for cartilage regeneration, it has an excellent ability to respond to a magnetic field, and it is much easier to precisely place the microstructure to a lesion of a patient and the microstructure provides a higher therapeutic effect.

The therapeutic agent of cartilage may be prepared by appropriate adjustment according to the purpose of the researcher or the conditions of the lesion. However, for the optimal treatment of cartilage, it is preferred that 100 µg/mL of magnetic substances be added to cells for cartilage regeneration ($1 \times 10^5$ cells/mL) and co-cultured. In particular, as the cells for cartilage regeneration, chondrocytes or stem cells that can be differentiated into cartilage may be used, and as the stem cells, adipose-derived stem cells, umbilical cord blood-derived stem cells, or bone marrow-derived stem cells may be used.

Figure 2A:
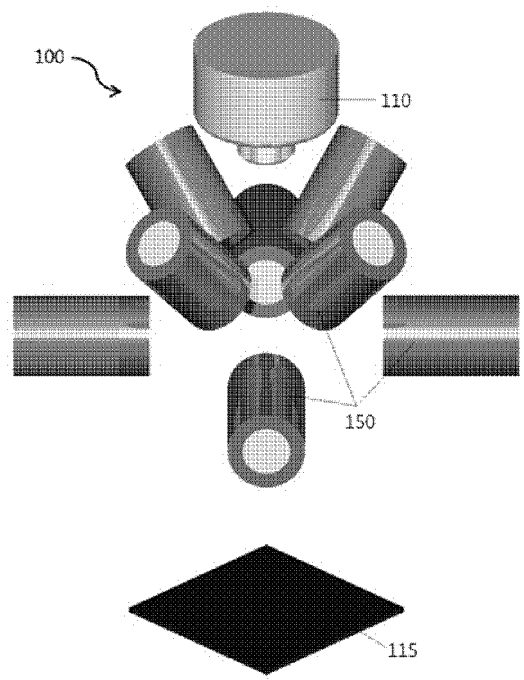
FIG. 2A shows a configuration diagram illustrating a magnetically-actuated articular cartilage regeneration system including a coil-type magnetic field forming unit according to an embodiment of the present invention.

FIG. 2A shows a schematic diagram illustrating a magnetically-actuated articular cartilage regeneration system 100 according to an embodiment of the present invention. As shown in FIG. 2A, an image-photographing unit 110 for irradiating X-ray to a lesion of the patient is formed at the upper part; a detector 115 for detecting X-ray as an image is formed at the bottom part; and a coil-type magnetic field forming unit 150, which consists of 8 coil-type electromagnetic field forming devices for accurately placing the magnetic substances contained in the therapeutic agent for cartilage administered to the lesion, is formed at the central part. The magnetically-actuated articular cartilage regeneration system 100 obtains a real-time three-dimensional image through X-ray in the image-photographing unit 110 and the detector 115 after administering a therapeutic agent for cartilage treatment to the knee, and thereby the position of the magnetic substances included in the therapeutic agent for cartilage treatment prepared according to an embodiment of the present invention and the exact position of the lesion can be identified, and the therapeutic agent for cartilage treatment can be precisely located to the defected area of cartilage through control of magnetic field using the coil-type the magnetic field forming unit 150. It is important to produce a magnetic field with higher intensity so as to more precisely locate the therapeutic agent for cartilage treatment, compared to the conventional ones, in which magnetic substances are included to a lesion. For this purpose, each electromagnetic field forming device, being comprised of a coil-type (i.e., a shape where an electromagnetic coil surrounds a core comprised of soft magnet), has a magnetic field with high intensity and is able to freely control the intensity and direction of the magnetic field. Additionally, such a magnetic field forming device can control the intensity and direction of a magnetic field using the outer permanent magnet configuration and control of positions. Accordingly, the treatment of articular cartilage can be maximized based on the imaging of the image-photographing unit 110 and the detector 115.

Figure 2B:
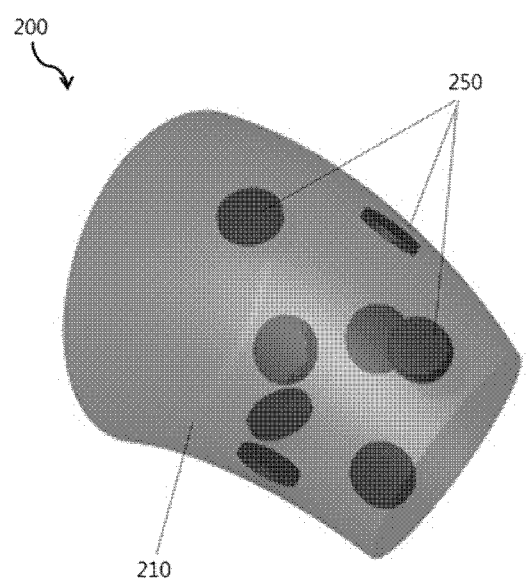
FIG. 2B shows a configuration diagram illustrating a magnetically-actuated articular cartilage regeneration apparatus including a wearable magnetic field forming device according to an embodiment of the present invention.

For the exhibition of characteristics of the present invention and optimal magnetic field forming effect for the treatment of articular cartilage, the coil-type magnetic field forming unit 150 of the present invention consists of eight coil-type electromagnetic field forming devices, however, the number and shape of these devices can also be appropriately adjusted according to the objects of the researcher and the position of the lesion. After the area and position for treatment of a therapeutic agent for cartilage treatment by the coil-type magnetic field forming unit 150 are identified, as shown in FIG. 2B, the efficiency of cartilage treatment is sought by wearing a wearable magnetic field forming device 200, not a coil-type, and the wearable magnetic field forming device 200 is composed of a wearable device 210 for wearing it on the knee considering convenience, and a plurality of permanent magnets 250 are formed inside of the device so as to generate a magnetic field with regard to the magnetic substances of the administered therapeutic agent for cartilage treatment. In particular, the permanent magnet 250 may be ferrite, neodymium, alnico, samarium cobalt, or rubber magnet.

The treatment process of cartilage regeneration using the coil-type magnetic field forming unit 150 according to the administration of a therapeutic agent for cartilage treatment (single cells or a cell structure) according to an embodiment of the present invention will be explained in detail in FIGS. 3A and 3B.

Figure 3A:
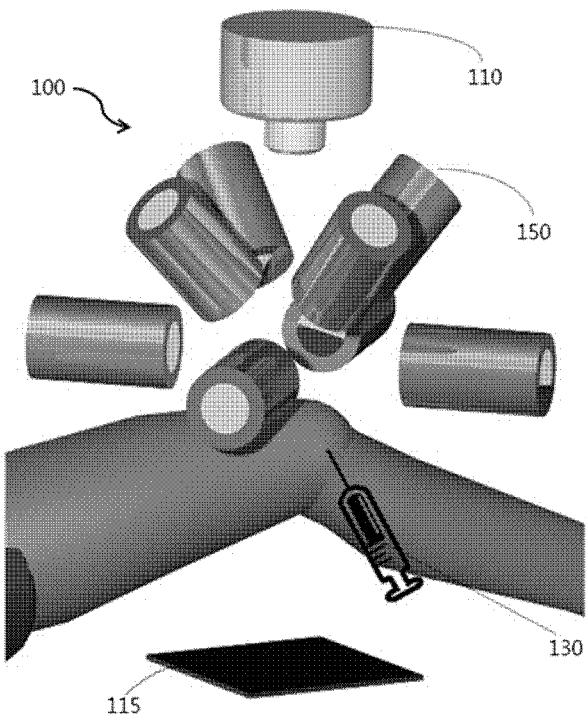
FIG. 3A shows a configuration diagram illustrating the process of treating articular cartilage using a magnetically-actuated articular cartilage regeneration system 100 according to an embodiment of the present invention.

FIG. 3A represents a schematic diagram illustrating the process of treating articular cartilage using the magnetically-actuated articular cartilage regeneration system 100 according to an embodiment of the present invention. First, a therapeutic agent for cartilage treatment 130, which is in the form of single cells for cartilage regeneration where magnetic substances are bound to single cartilage regeneration cells, or a cell structure for cartilage regeneration in a spheroid shape where magnetic substances are three-dimensionally bound to multiple cells for cartilage regeneration, is administered to a lesion of a patient using a syringe; the image-photographing unit 110 irradiates x-ray on the lesion, which is embodied as a three-dimensional real-time imaging through the detector 115, and thereby the location of the administered single cells or cell structure can be identified. In particular, the intensity of the magnetic field is controlled so that the single cells or cell structure can move close to the defected area of the patient's cartilage by actuating the coil-type magnetic field forming unit 150 based on the photographed three-dimensional real-time imaging, and the administered single cells or cell structure can be precisely located to the defected area of cartilage lesion by controlling the intensity of all or part of the magnetic field of the coil-type magnetic field forming unit 150. The intensity of the magnetic field of the coil-type magnetic field forming unit 150 may be formed within a range of about 1,000 mT, and it is preferred that the magnetic intensity be controlled by utilizing the same in appropriate cartilage treatment.

Figure 3B:
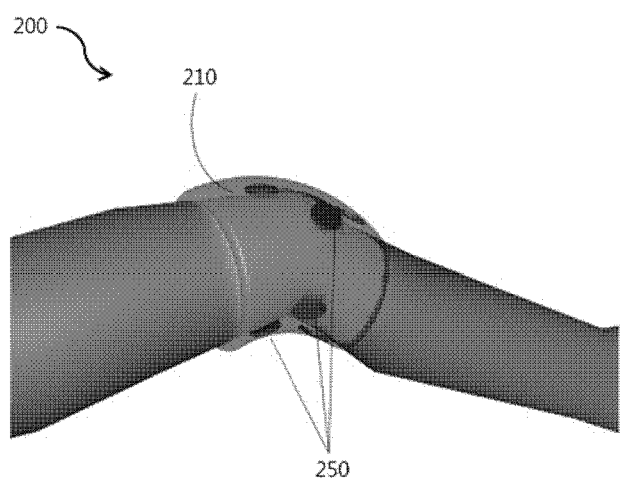
FIG. 3B shows a schematic diagram illustrating an image where a wearable magnetic field forming device according to an embodiment of the present invention is worn onto a defected area of cartilage.

Additionally, FIG. 3B shows an image in which the wearable magnetic field forming device 200 according to an embodiment of the present invention is worn on a cartilage lesion. As described above, the wearable magnetic field forming device 200 is worn so as to fix the magnetic field forming position for a lesion based on the area of treatment identified previously by controlling the direction and intensity of magnetic field of the coil-type magnetic field forming unit 150 using the magnetically-actuated articular cartilage regeneration system 100. The wearable magnetic field forming device 200 can be directly worn by a patient on a lesion without a separate additional device and can be conveniently carried on. The magnetic substances (i.e., multiple permanent magnets 250 installed inside of the wearable device 210), included in the administered therapeutic agent for cartilage treatment (single cells or a cell structure) are distributed in the most optimized location for treatment of a defected area of cartilage. Accordingly, the multiple permanent magnets 250 installed inside of the wearable device 210 may be densely distributed to a single lesion or dispersedly distributed considering the efficiency of treatment.

Figure 4:
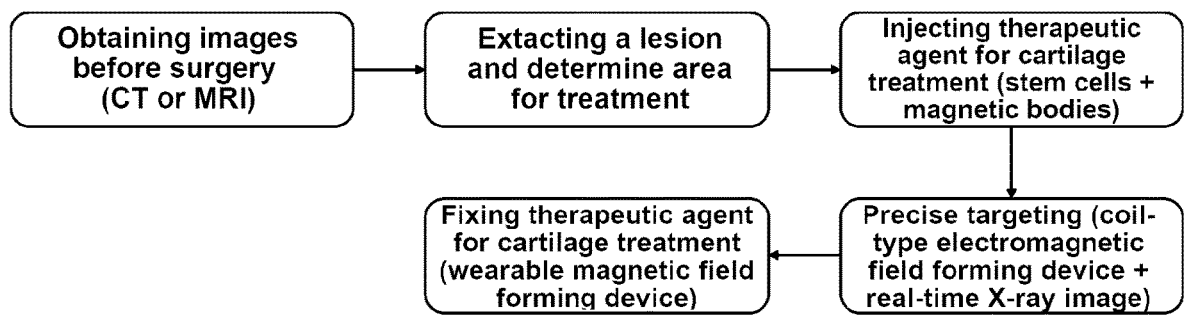
FIG. 4 shows a flow chart illustrating the process of treating a lesion using a therapeutic agent for cartilage treatment, a coil-type electromagnetic field forming device, and a wearable magnetic field forming device according to an embodiment of the present invention.

FIG. 4 shows a schematic diagram illustrating the process of treating defected cartilage using the magnetically-actuated articular cartilage regeneration system 100 according to an embodiment of the present invention. As illustrated, first, the obtained 3D images (e.g., CT, MRI images, etc.) of a patient on the articular lesion are analyzed before surgery, the lesion is extracted, and thereby the area for treatment is determined. Then, a therapeutic agent for cartilage treatment, in which cells for cartilage regeneration (i.e., stem cells or chondrocytes) are bound to magnetic substances, are administered to the periphery of treatment area using a syringe, etc. and the therapeutic agent for cartilage treatment 130 in the form of single cells or a cell structure may be administered according to the severity and location of the lesion. Subsequently, based on the image information obtained through the image-photographing unit 110 and the detector 115, the coil-type magnetic field forming unit 150 is actuated to control the direction and intensity of the formed magnetic field are controlled in real-time, and thereby the therapeutic agent for cartilage treatment 130 is precisely delivered to the area for treatment. Finally, the distribution of the delivered therapeutic agent for cartilage treatment 130 within the area for treatment is examined, and the location and distribution of the permanent magnet 250 of the wearable magnetic field forming device 200 are fixed thereby enhancing the efficiency of long-term articular cartilage treatment.

Hereinafter, the present invention will be described in more detail through examples. However, the present invention is not limited to these examples described below, but may be implemented in various other forms, and the following examples are provided to complete the disclosure of the present invention and to fully disclose the scope of the invention to those skilled in the art.

Example 1: Manufacture of PLGA Micro-Scaffold Body

A PLGA micro-scaffold body was prepared by the double emulsion method using a fluidic device with a slightly modified process according to an embodiment of the present invention.

Specifically, the fluidic device was comprised of a PVE tube (1/32 in i.d.×3/32 in o.d.), a 21 G needle, and a syringe pump, and a two-way flow channels device was manufactured by inserting a needle to the PVC tube. First, for the W-O emulsion, PLGA solutions and gelatin solutions were prepared. For the preparation of the solutions, PLGA (85 mg/mL) was dissolved in 100 mL PVA 5%, aqueous gelatin (0.1 g/ml) solution, and 1 mL dichloromethane (DCM)/Span80 (100:1, v/v) solution, respectively, and the W-O emulsion was prepared by mixing with the gelatin solution (0.55-0.85 mL, 0.1 mL interval, optimized value: 0.65 mL) in the PLGA solution at 2500 rpm for 2 minutes 30 seconds. The W-O emulsion was filled into a syringe with a 26 G needle, and the needle of the syringe was inserted into the center of the 21 G needle of the fluidic device formed of PVA 1% with a flow rate of 3 mL/min passing continuously through the PVC tube of the fluidic device. Then, the W—O-W droplets formed in the fluidic channel were flowed along the 21 G needle of the fluidic device, and collected into deionized water in which a 500 mL beaker in an ice bath is located. Subsequently, the dichloromethane in the collected droplets was evaporated while gently stirring for 6 hours, and for the removal of gelatin of the droplets, the resultant was immersed in the 500 mL beaker with deionized water at 37° C., and gently stirred for 4 hours. Finally, the droplets were washed 3 times with deionized water, and the gelatin-leached PLGA scaffold body was stored in deionized water in a 25 mL vial.

Figure 1B:
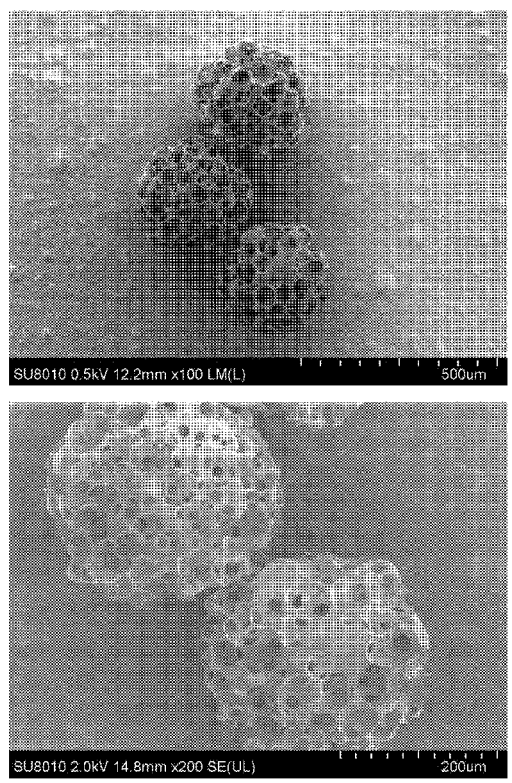
FIG. 1B shows images illustrating microstructures obtained through the above manufacturing process photographed under a scanning electron microscope (the upper scale: 500 µm, and the lower scale: 200 µm in scale unit)

The PLGA micro-scaffolds manufactured above was photographed using a scanning electron microscope. As a result, it was confirmed that the micro-scaffolds in a spherical shape with multiple pores formed thereon were normally formed as shown in FIG. 1B.

Figure 1C:
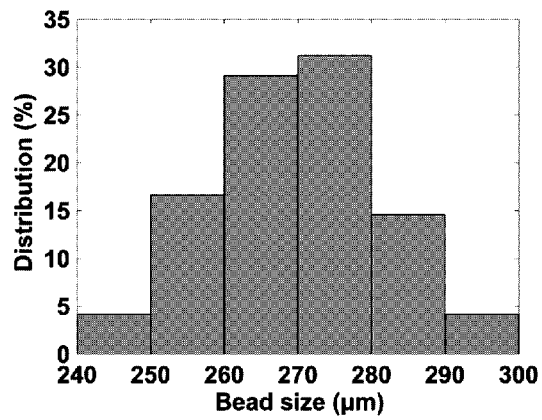
FIG. 1C shows a histogram illustrating the distribution of diameters of a microstructure for cartilage regeneration manufactured according to an embodiment of the present invention.
Figure 1D:
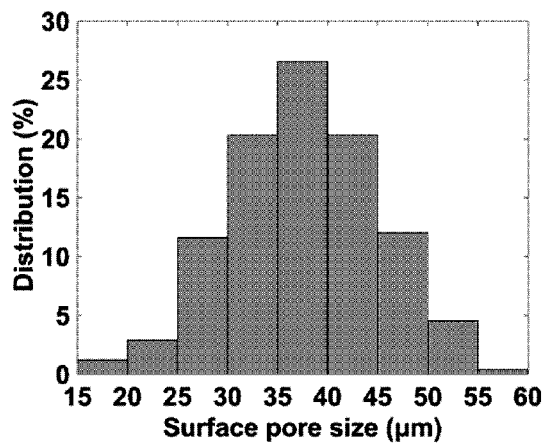
FIG. 1D shows a histogram illustrating the size distribution of surface pores of a microstructure for cartilage regeneration manufactured according to an embodiment of the present invention.
Figure 1E:
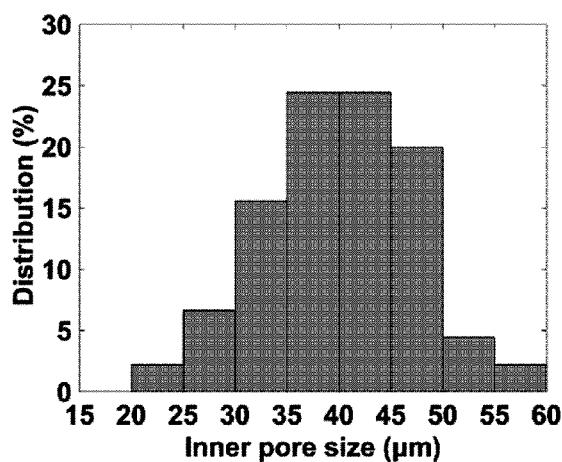
FIG. 1E shows a histogram illustrating the size distribution of inner pores of a microstructure for cartilage regeneration manufactured according to an embodiment of the present invention.

Additionally, the present inventors analyzed the distribution of the diameter, and the size of outer pores and inner pores of the PLGA micro-scaffolds manufactured above. As a result, it was confirmed that the diameter was 269.83±10.982 μm, the diameter of the surface pores was 37.68±7.55 μm, the diameter of the inner pores was 40.12±7.45 μm; and as shown in FIGS. 1C to 1E, it was confirmed that 90% or more of the scaffolds had a diameter of 250 m to 290 μm, 90% or more of the surface pores had a size of 23 m to 50 μm, and 90% or more of the inner pores had a size of 25 μm to 50 μm, thus showing a normal distribution pattern. Such a distribution of relatively uniform diameter and the size of surface and inner pores shows that the PLGA micro-scaffold according to an embodiment of the present invention can be efficient as a cell transporter. In fact, the above results satisfy the conditions of the microstructure as a cell transporter (diameter of 100 μm to 500 μm; and pore size of m or greater) (Choi et al., J. Mater. Chem. 22: 11442, 2012).

Example 2: Preparation of Amine-Functionalized Magnetic Nanoparticles

Amine-functionalized $Fe_3O_4$ MNPs for providing an electromagnetic actuation ability to the scaffold body manufactured in Example 1 according to an embodiment of the present invention was manufactured.

Specifically, in order to modify the surface of MNPs for the high-efficiency gene transfer by the proton sponge effect among the biocompatible materials having an amine group, polyethylenimine (PEI) was selected. First, 10 mM ferric chloride and 5 mM ferrous chloride were dissolved in 1 M HCl solution (12 mL), and the mixed solution was added to 1 M sodium solution (50 mL) in a four-neck round flask with a mechanical stirrer. The reaction solution was heated at 80° C. in a dry nitrogen atmosphere, vigorously stirred for 2 hours, and formed $Fe_3O_4$ MNPs in the above step and precipitated at the bottom of the flask. Then, PEI (10 g) was added to the $Fe_3O_4$ solution, and the solution was heated at 90° C. and maintained thereat for 1 hour. The PEI precipitant coated with the MNPs was washed 5 times with deionized water and dispersed in an aqueous solution.

Example 3: Manufacture of Micro-Scaffold to which Magnetic Nanoparticles are Attached In order to attach the PEI coated with the $Fe_3O_4$ MNPs manufactured in Example 2 to the surface of the PLGA micro-scaffold according to an embodiment of the present invention, a coupling process using the amino bond formation was used. First, the PLGA scaffold was immersed in 0.1 M MES solution (5 mL) supplemented with 1.5 mM N-hydroxysuccinimide (NHS) and 1-ethyl-(dimethylaminopropyl) carbodiimide (EDC) at 33° C., and the solution containing the micro-scaffold was mechanically stirred for 6 hours so as to activate carboxyl groups on the surface of the PLGA micro-scaffold. After the activation of the micro-scaffold surface, the PEI, where the MNPs (10 mg/mL) modified in 0.1 M MES (5 mL) were dispersed, was added to the solution, and stirred at 33° C. for 12 hours. Then, the solution was filtered to remove unreactive MNPs and the MNPs of the micro-scaffold fixed to the filter were collected and washed three times with deionized water.

Example 4: Manufacture and Cultivation of Micro-Scaffold to which Stem Cells are Loaded The micro-scaffold, to which magnetic nanoparticles (MNPs) are attached, manufactured in Example 3 was immersed in DMEM medium containing 10% FBS, and mouse bone marrow-derived mesenchymal stem cells (MSC) ($1\times10^6$ cells/scaffold) were injected onto the micro-scaffold under a microscope, and cultured in an incubator with 5% $CO_2$ at 37° C. The medium was replaced every two days and the mesenchymal stem cells were allowed to settle in the micro-scaffold. In particular, as the control group, mesenchymal stem cells at the same concentration were injected to a micro-scaffold to which magnetic nanoparticles (MNPs) are not attached.

The mesenchymal stem cells, which were introduced into a micro-scaffold, were cultured in a incubator with 5% $CO_2$ at 36° C. as described above, and simultaneously, the number of cells was measured using the Cell Titer 96 Cell Proliferation Assay kit (Promega, USA).

Figure 5A:
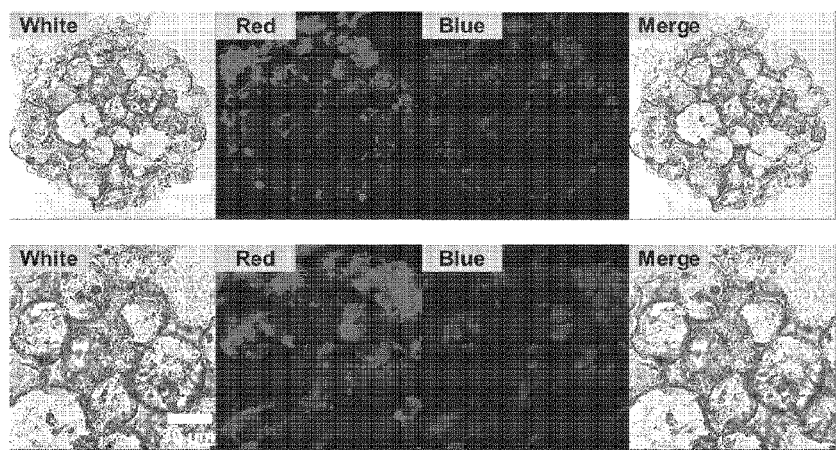
FIG. 5A shows images illustrating a magnetic nanoparticles-coated micro-scaffold where stem cells are supported according to an embodiment of the present invention by a confocal laser microscope (the images in the lower part are enlarged images of those in the upper part)
Figure 5B:
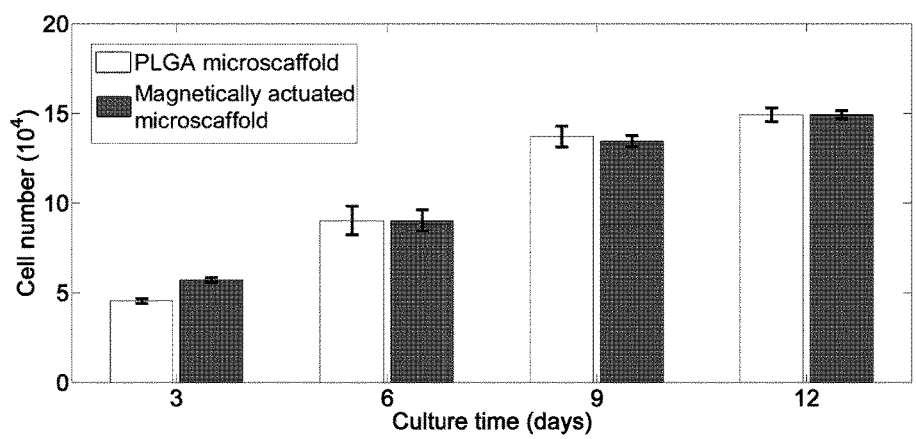
FIG. 5B shows a graph illustrating the analysis results of the stem cell proliferation ability in the micro-scaffold where stem cells are supported.
Figure 6:
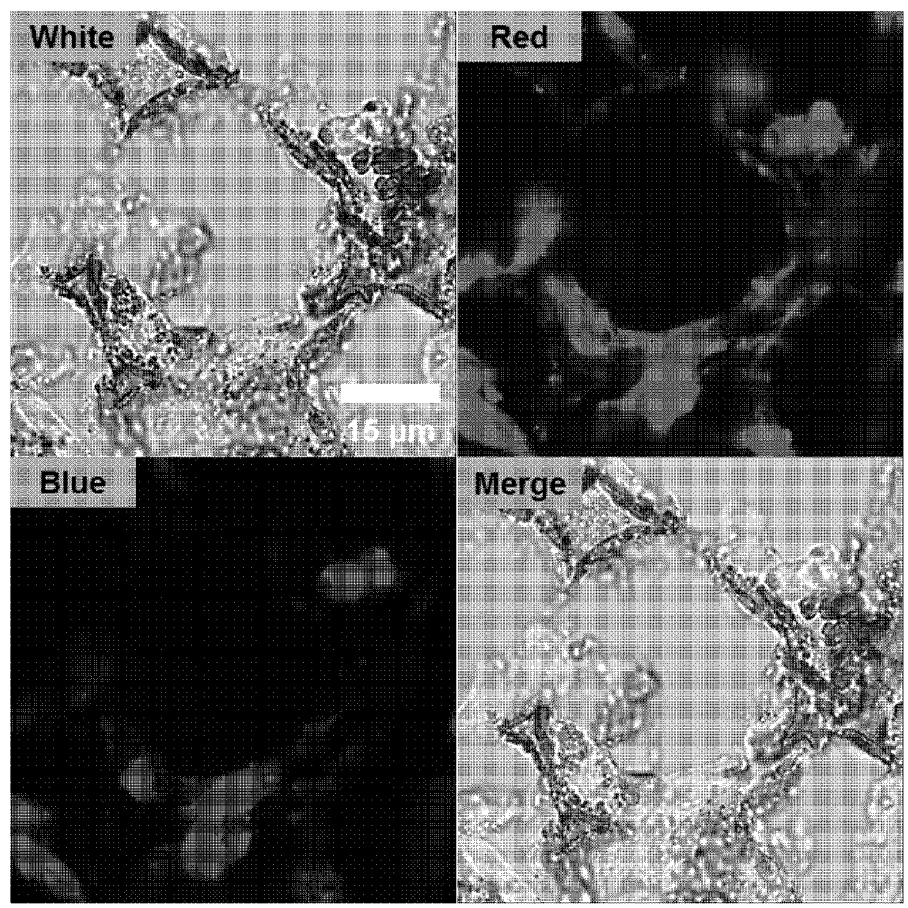
FIG. 6 shows images illustrating the shapes of stem cells within the micro-scaffold according to an embodiment of the present invention by a confocal laser microscope.
Figure 7A:
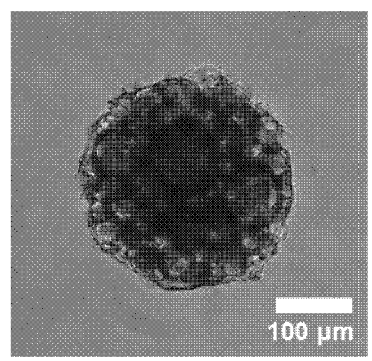
FIG. 7A shows an image illustrating the PLGA micro-scaffold photographed by an optical microscope.
Figure 7B:
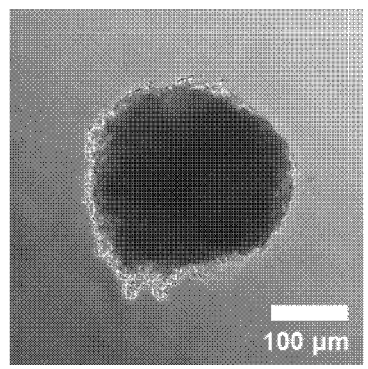
FIG. 7B shows an image illustrating the PLGA micro-scaffold, where the mesenchymal stem cells of FIG. 7A are loaded, photographed by an optical microscope after placing the PLGA micro-scaffold in a medium for differentiation of chondrocytes for 21 days followed by Alcian blue staining.
Figure 7C:
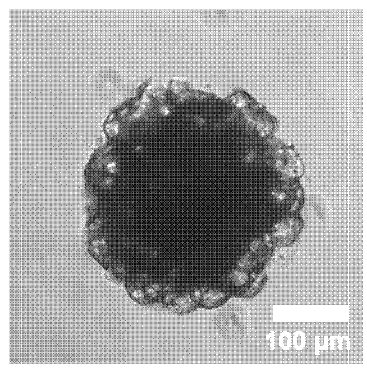
FIG. 7C shows an image illustrating a magnetic nanoparticles-coated micro-scaffold according to an embodiment of the present invention photographed by an optical microscope.
Figure 7D:
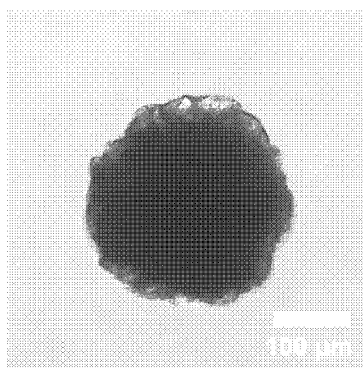
FIG. 7D shows an image illustrating the magnetic nanoparticles-coated PLGA micro-scaffold, where the mesenchymal stem cells of FIG. 7C are loaded, photographed by an optical microscope after placing the PLGA micro-scaffold in a medium for differentiation of chondrocytes for 21 days followed by Alcian blue staining.
Figure 7E:
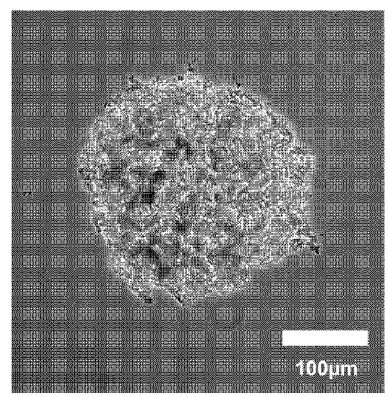
FIG. 7E shows an image illustrating the magnetic nanoparticles-coated PLGA micro-scaffold photographed by an optical microscope after segmentation of the magnetic nanoparticles-coated PLGA micro-scaffold following the differentiation of chondrocytes of FIG. 7D, followed by Alcian blue staining.
Figure 7F:
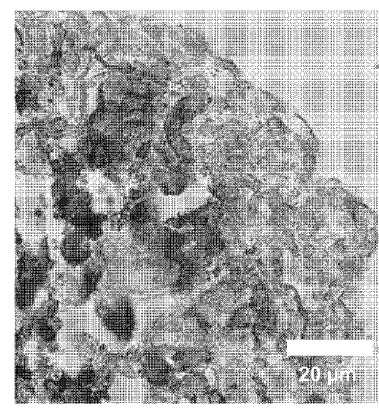
FIG. 7F shows an enlarged image of a part of the image of FIG. 7E.

As a result, as shown in FIGS. 5A and 5B, it was confirmed that both micro-scaffolds into which the magnetic nanoparticles were introduced or not introduced, were normally grown. As a result of confirming the detailed structure of the micro-scaffolds by increasing the magnification of the microscope, it was confirmed that stem cells penetrated into the inner pores of the micro-scaffolds. Interestingly, on the $3^{rd}$ day of the cultivation, the micro-scaffold into which the magnetic nanoparticles were introduced showed a higher growth rate of the mesenchymal stem cells compared to that of the control group, where the mesenchymal stem cells were cultured in a normal PLGA micro-scaffold.

Example 5: Experiment of Confirming Differentiation Ability of Stem Cells

The present inventors have examined the differentiation ability of the mesenchymal stem cells, in order to confirm whether the mesenchymal stem cells, which are attached to the micro-scaffold structure manufactured in Example 4 can be able to differentiate into chondrocytes.

Specifically, a culture dish, in which the magnetic nanoparticles-coated micro-scaffold structure manufactured in Example 4 into which mesenchymal stem cells are introduced is contained, was treated with a medium for differentiation into chondrocytes consisting of DMEM medium (StemPro Chondrocyte Differentiation Kit, Thermo Fisher Scientific, USA) containing glucose (4.5 g/L), 1% ITS (insulin (25 µg/mL), transferrin (25 µg/mL), and sodium selenite (25 ng/mL), $0.1\times10^{-6}$ M dexamethasone, L-ascorbic acid-2-phophosphate (50 µg/mL), and TGF-β1 (10 µg/mL). After 21 days, the cells were stained with Alcian Blue and the degree of differentiation of the cells into chondrocytes were observed. Part of the micro-scaffold was prepared into frozen sections and stained with Alcian Blue.

As a result, as shown in FIGS. 7A to 7F, it was confirmed that the bone marrow-derived mesenchymal stem cells settled in the micro-scaffold were differentiated into chondrocytes.

Figure 8:
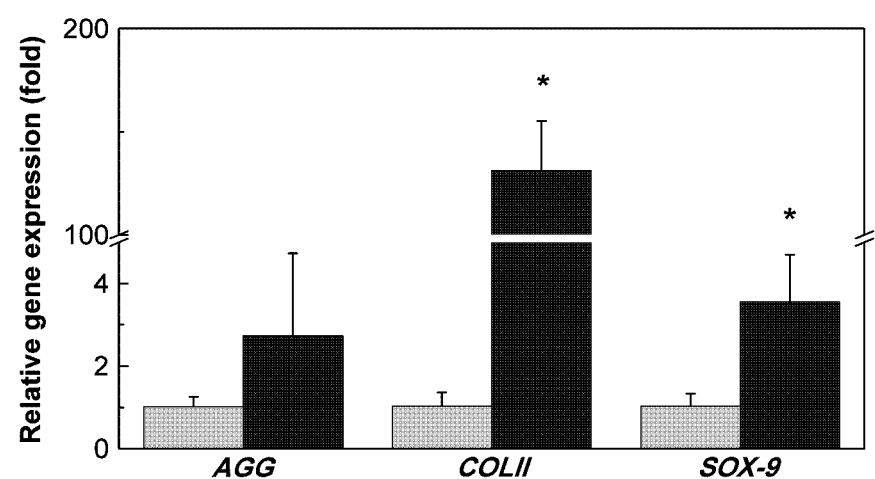
FIG. 8 shows a graph illustrating the analysis results of the relative expression levels of chondrocytes differentiation-related markers (AGG, COL2A1, and SOX-9) compared to those of the undifferentiated control group, after the induction of differentiation of the stem cells cultured in the micro-scaffold according to an embodiment of the present invention.

Furthermore, in order to observe the degree of differentiation into chondrocytes, the present inventors have analyzed the expression levels of marker genes (i.e., Aggrecan (AGG), collagen 2A1 (COL2A1), and SOX9) related to differentiation into chondrocytes using qRT-PCR (FIG. 8). Specifically, the magnetic nanoparticles-coated micro-scaffold was treated with medium for differentiation into chondrocytes, and after 21 days, the total RNA was extracted using an RNA extraction kit (TaKaRa MiniEST Universal RNA Extraction Kit, Takara, Japan), and the extract was subjected to reverse transcription using a reverse transcription kit (PrimeScript Master Mix, Takara, Japan), and then to qRT-PCR using 5X FIREPol, EvaGreen, and qPCR Supermix (Solis BioDyne, Estonia). As a result, as shown in FIG. 8, the mesenchymal stem cells loaded in the differentiation-induced magnetic nanoparticles-coated micro-scaffold showed higher expression levels of marker genes related to differentiation into chondrocytes compared to the control group where differentiation was not induced. Accordingly, it was confirmed that the magnetic nanoparticles-coated micro-scaffold according to an embodiment of the present invention can normally induce the differentiation of mesenchymal stem cells into chondrocytes.

Example 6: Experiment on 2D Magnetic Actuation

In order to confirm whether the micro-scaffold mesenchymal stem cell complex into which magnetic nanoparticles (MNPs) are introduced according to an embodiment of the present invention is able to control migration, a two-dimensional (2D) magnetic actuation was performed.

Figure 9A:
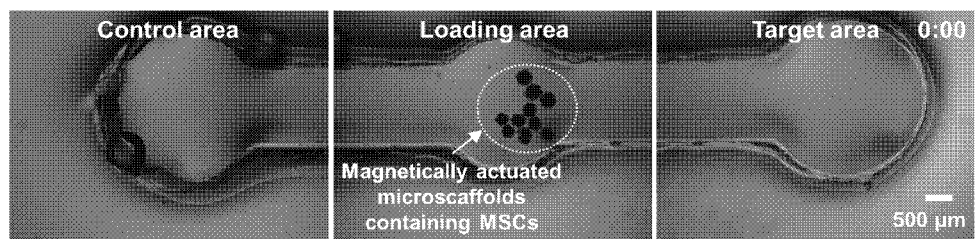
FIG. 9A shows microscopic images illustrating the measured magnetic actuation ability of a micro-scaffold for a target area by performing a 2D targeting ability test according to an embodiment of the present invention.

Specifically, a mold for a PDMS chamber was manufactured by attaching a dumbbell-type structure to a glass substrate using a 3D printer. Then, a PDMS polymer was prepared by mixing a curing agent and a PDMS precursor in a ratio of 10:1 was casted into a mold, and a PDMS block was attached to a slide glass using a plasma, and the prepared chamber was divided into three domains (i.e., control, loading, and target areas) (FIG. 9A). Subsequently, 10 magnetic nanoparticles-loaded micro-scaffold (manufactured in Example 4) MSC complexes were loaded into the loading area of the microfluidic chamber, and placed on the workbench of an EMA system, in which an inverted microscope is installed, that can confirm the optical image and fluorescent image of the micro-scaffold MSC complex within the microfluidic chamber in real-time, and observed.

Figure 9B:
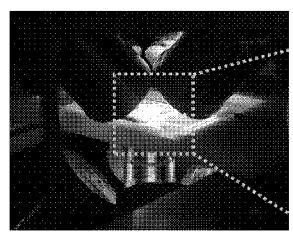
FIG. 9B shows a photograph illustrating a magnetic actuation (EMA) system used in the magnetic actuation of a micro-scaffold mesenchymal stem cell complex of the present invention.

The EMA system was tested as described below using a magnetically-actuated system (FIG. 9B) consisting of a permanent magnet comprised of four cylindrical neodymium magnets (diameter 10 mm×height 20 mm) with a magnetization value of 955 kA/m. The micro-scaffold was loaded into the loading section in the microfluidic chamber of a PDMS material in which glycerin (70 wt %) solution, which has a viscosity at room temperature is similar to that of the synovial fluid, is supported; and then the microfluidic chamber was placed on the workbench of a magnetically-actuated system A, and the fixed uniform magnetic field (30 mT) and variable magnetic gradient field (0.2-1.2 T/m, interval 0.2 T/m) were produced in the EMA system along each of x and z axes, and the micro-scaffold was promoted toward the direction of the gradient magnetic field. Finally, to obtain the velocity, the recorded locomotion was analyzed.

Figure 9C:
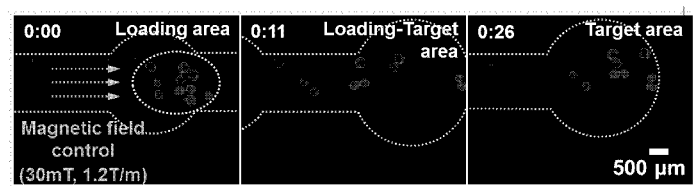
FIG. 9C shows photographed images illustrating the measured magnetic actuation ability of a micro-scaffold for a target area by performing a 2D targeting ability test according to an embodiment of the present invention.

As a result, as shown in FIG. 9C, 9 out of the 10 micro-scaffolds were moved to the target area, and it was confirmed that the micro-scaffolds were induced with regard to the target area through the control of the magnetic field.

Example 8: Test of 3D Targeting Ability

Figure 10:
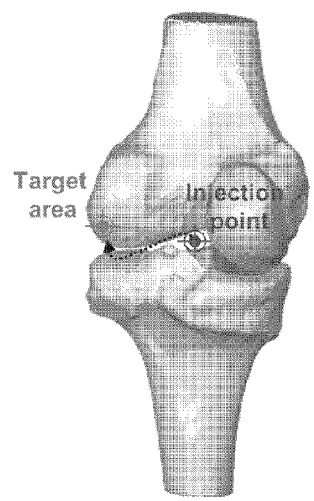
FIG. 10 shows an image illustrating a knee phantom model for a 3D targeting ability test according to an embodiment of the present invention.

The targeting ability of the magnetically-actuated micro-scaffold manufactured according to an embodiment of the present invention to the defected area of the joint was observed. First, the knee phantom for the test of 3D targeting ability was manufactured from a 3D CAD model of a knee using a 3D printer (FIG. 10). Then, apertures with a depth of 3 mm and a diameter of 2 mm were formed toward the target area inside of the femur, and the above model manufactured for the test of 3D targeting ability was placed in the acrylic chamber filled with glycerin solution (70 wt %) Then, 5 micro-scaffolds were injected between the defected areas of the joint of the knee model phantom by pipetting, and the locomotion into the target domain was observed.

Figure 11:
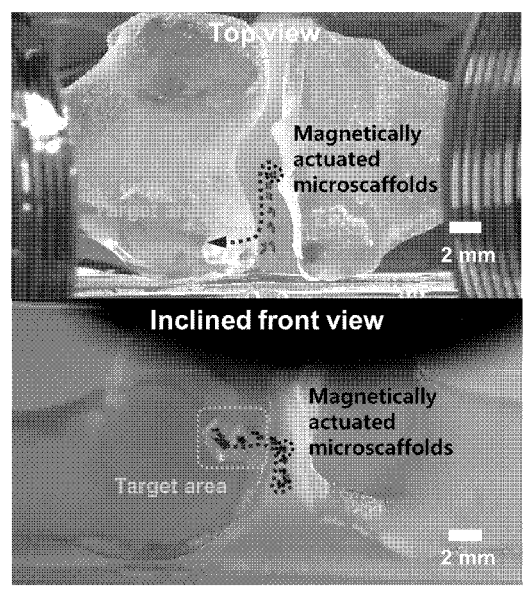
FIG. 11 shows an image illustrating the potential of a targeting ability of a micro-scaffold in a 3D targeting ability test using the knee phantom model according to an embodiment of the present invention.

As a result, it was confirmed that 5 micro-scaffolds with a similar velocity moved from the injected position to the target domain and thus the targeting ability of the micro-scaffolds were possible in the test of 3D targeting ability (FIG. 11).

Conclusively, the use of the magnetically-actuated articular cartilage regeneration system 100 of the present invention, after the administration of a therapeutic agent for cartilage treatment containing magnetic substances, can control the intensity of magnetic field and precisely locate and fix the therapeutic agent for cartilage treatment to a lesion based on the real-time image information, thereby promoting nonsurgical and efficient effect of cartilage treatment.

While the present invention has been described with reference to the foregoing examples, it is apparent to those skilled in the art that these examples are only for illustrative purposes and various modifications and equivalent embodiments are possible without departing from the scope of the present invention. Accordingly, the true scope of the present invention should be determined by the technical idea of the appended claims.

INDUSTRIAL APPLICABILITY

The composition for regenerating cartilage may be effectively used for the treatment of other diseases due to cartilage damage such as osteoarthritis.

The invention claimed is:

1. A composition for regenerating cartilage comprising a porous microstructure to which at least one magnetic nanoparticle and at least one cartilage-producing cell are attached,
    wherein the at least one magnetic nanoparticle is amine-functionalized with a biocompatible material having at least one amine group attached to a surface of the porous microstructure,
    wherein the at least one cartilage-producing cell is allowed to settle by cultivation, and
    wherein the porous microstructure is made from a biodegradable polymer selected from the group consisting of collagen, hyaluronic acid, gelatin, chitosan, PLGA{poly(lactic-co-glycolic acid)}, PGA{poly(glycolic acid)}, PLA{poly(lactic acid)} and PEG(poyethylene glycol).

2. The composition of claim 1, wherein the cartilage-producing cell is a cartilage cell or stem cell.

3. The composition of claim 2, wherein the stem cell is a bone marrow-derived stem cell or fat-derived stem cell.

4. A magnetically-actuated articular cartilage regeneration system, comprising:
    a composition for regenerating cartilage of claim 1;
    an image-photographing unit for imaging the composition for regenerating cartilage and a lesion after irradiating x-ray on a defected area of cartilage; and
    a magnetic field forming unit for transporting the composition for regenerating cartilage to the defected area of cartilage.

5. The magnetically-actuated articular cartilage regeneration system of claim 4, wherein the magnetic field forming unit is a coil or is wearable.

6. The magnetically-actuated articular cartilage regeneration system of claim 5, wherein the transporting of the composition by the magnetic field forming unit is performed by an electromagnet or a permanent magnet.

7. The magnetically-actuated articular cartilage regeneration system of claim 6, wherein the permanent magnet is ferrite, neodymium, alnico, samarium cobalt, or a rubber magnet.

8. The magnetically-actuated articular cartilage regeneration system of claim 5, wherein the cartilage-producing cell is a chondrocyte or a stem cell.

9. The magnetically-actuated articular cartilage regeneration system of claim 8, wherein the stem cell is a fat-derived stem cell, an umbilical cord blood-derived stem cell or a bone marrow-derived stem cell.

* * * * *